United States Patent
Poinsard et al.

(10) Patent No.: US 9,120,753 B2
(45) Date of Patent: *Sep. 1, 2015

(54) PHENOL DERIVATIVES AND PHARMACEUTICAL OR COSMETIC USE THEREOF

(75) Inventors: Cédric Poinsard, Le Plan de Grasse (FR); Pascal Collette, Le Cannet (FR); Patrice Lucien Maurice Collette, legal representative, Igny (FR); Isabelle Marie Joëlle Martine Collette, legal representative, Alfortville (FR); Pascale Mauvais, Antibes (FR); Jean-Michel Linget, Benfeld (FR); Sandrine Rethore, Valbonne (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/519,113

(22) PCT Filed: Dec. 22, 2010

(86) PCT No.: PCT/FR2010/052872
§ 371 (c)(1),
(2), (4) Date: Oct. 9, 2012

(87) PCT Pub. No.: WO2011/077044
PCT Pub. Date: Jun. 30, 2011

(65) Prior Publication Data
US 2013/0172564 A1    Jul. 4, 2013

Related U.S. Application Data

(60) Provisional application No. 61/282,152, filed on Dec. 23, 2009.

(30) Foreign Application Priority Data

Dec. 23, 2009  (FR) ..................................... 09 59476

(51) Int. Cl.
| C07D 213/74 | (2006.01) |
| C07D 213/85 | (2006.01) |
| A61K 8/49 | (2006.01) |
| A61K 31/44 | (2006.01) |
| A61Q 19/00 | (2006.01) |
| A61Q 7/02 | (2006.01) |

(52) U.S. Cl.
CPC ............ *C07D 213/85* (2013.01); *A61K 8/4906* (2013.01); *A61K 8/4926* (2013.01); *A61K 31/44* (2013.01); *A61Q 19/00* (2013.01); *C07D 213/74* (2013.01); *A61Q 7/02* (2013.01); *A61Q 19/008* (2013.01)

(58) Field of Classification Search
CPC ..... C07D 213/74; C07D 213/85; A61K 31/44
USPC .................................. 546/297; 514/352, 357
See application file for complete search history.

(56) References Cited

U.S. PATENT DOCUMENTS

| 4,578,390 A | 3/1986 | Jensen et al. |
| 2013/0178633 A1* | 7/2013 | Poinsard et al. ............... 546/297 |
| 2014/0275536 A1* | 9/2014 | Poinsard ....................... 544/317 |

FOREIGN PATENT DOCUMENTS

| AU | 670942 B2 | 8/1996 |
| EP | 0580459 A1 | 1/1994 |
| WO | 2005/042464 A1 | 5/2005 |
| WO | 2006/010637 A2 | 2/2006 |

OTHER PUBLICATIONS

Dorwald; Side Reactions in Organic Synthesis, 2005, Wiley-VCH, Weinheim, chapter 1, pp. 1-16.*
International Search Report issued on May 27, 2011 by the European Patent Office as the International Searching Authority in International Patent Application No. PCT/FR2010/052872, and an English language translation of the Search Report.

* cited by examiner

Primary Examiner — John Mabry
Assistant Examiner — Daniel Carcanague
(74) Attorney, Agent, or Firm — Dentons US LLP

(57) ABSTRACT

The use of compounds in the treatment of skin disorders is described. In particular, use of a compound of formula (I):

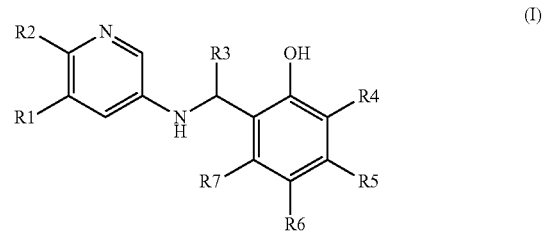

or one of its pharmaceutically acceptable salts, solvates or hydrates in the preparation of a medicament to treat skin pathologies is described.

14 Claims, No Drawings

PHENOL DERIVATIVES AND PHARMACEUTICAL OR COSMETIC USE THEREOF

CROSS-REFERENCE TO PRIOR APPLICATIONS

This application is a National Stage of PCT/FR2010/052872, filed Dec. 22, 2010, and designating the United States (published in French on Jun. 30, 2011, as WO 2011/077044 A2; the title and abstract were published in English), which claims priority of FR 0959476, filed Dec. 23, 2009, and U.S. Provisional Patent Application No. 61/282,152, filed Dec. 23, 2009, each hereby expressly incorporated by reference in its entirety and each assigned to the assignee hereof.

The present invention relates to novel compounds of general formula:

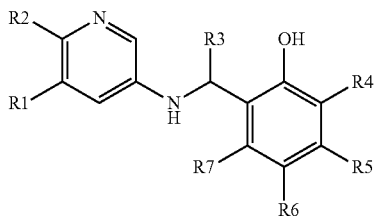

and to the cosmetic or pharmaceutical use thereof.

The present invention proposes to provide novel phenolic derivatives which are powerful androgen receptor modulators.

Among the prior art documents describing molecules which modulate androgen receptor activity, mention may, for example, be made of the phenylimidazolines described in patent application EP 580 459, or application WO 2005/42464.

The invention relates to novel phenolic derivatives that correspond to general formula (I) below:

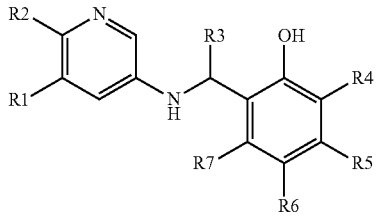

in which:

$R_1$ represents a $C_{1-6}$ alkyl, $C_{3-7}$ cycloalkyl, $C_{1-6}$ alkyloxy, —S(O)$_m$—$C_{1-6}$ alkyl, $C_{1-6}$ fluoroalkyl, $C_{1-6}$ fluoroalkyloxy, —(CH$_2$)$_n$—$C_{3-9}$ cycloalkyl, —(CH$_2$)$_n$—$C_{3-9}$ cycloalkyl, $C_{2-6}$ alkyl-OH, —(CH$_2$)$_n$—$C_{1-6}$ alkyloxy, —(CH$_2$)$_n$—$C_{1-6}$ fluoroalkyl, —(CH$_2$)$_p$—O—$C_{1-6}$ fluoroalkyl, COR$_a$, CN, NO$_2$ or NR$_8$R$_9$ group, a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different $R_b$ groups, $R_2$ represents a $C_{1-6}$ alkyl, $C_{3-7}$ cycloalkyl, $C_{1-6}$ alkyloxy, —S(O)$_v$$C_{1-6}$ alkyl, $C_{1-6}$ fluoroalkyl, $C_{1-6}$ fluoroalkyloxy, —(CH$_2$)$_q$—$C_{3-9}$ cycloalkyl, —(CH$_2$)$_q$—$C_{3-9}$ cycloalkyl, $C_{2-6}$ alkyl-OH, —(CH$_2$)$_q$—$C_{1-6}$ alkyloxy, —(CH$_2$)$_q$—$C_{1-6}$ fluoroalkyl, —(CH$_2$)$_t$—O—$C_{1-6}$ fluoroalkyl, COR$_d$, CN, NO$_2$ or NR$_8$'R$_9$' group, a hydrogen atom, a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different $R_e$ groups, $R_3$ represents a hydrogen atom or a $C_{1-9}$ alkyl, $C_{3-9}$ cycloalkyl, $C_{1-6}$ fluoroalkyl, —(CH$_2$)$_t$—$C_{3-9}$ cycloalkyl, —$C_{2-6}$ alkyl-OH, —(CH$_2$)$_u$—$C_{1-6}$ alkyloxy, —(CH$_2$)$_t$—$C_{3-7}$ cycloalkyl, —(CH$_2$)$_t$—$C_{1-6}$ fluoroalkyl, or —(CH$_2$)$_u$—O—$C_{1-6}$ fluoroalkyl group, $R_4$, $R_5$, $R_6$ and $R_7$ are identical or different and represent either a hydrogen atom or a $C_{1-6}$ alkyl, $C_{3-7}$ cycloalkyl, $C_{1-6}$ alkyloxy, —S(O)$_i$—$C_{1-6}$ alkyl, $C_{1-6}$ fluoroalkyl, $C_{1-6}$ fluoroalkyloxy, —(CH$_2$)$_i$—$C_{3-9}$ cycloalkyl, —(CH$_2$)$_i$—$C_{3-9}$ cycloalkyl, —$C_{1-6}$ alkyl-OH, —(CH$_2$)$_i$—$C_{1-6}$ alkyloxy, —(CH$_2$)$_i$—$C_{1-6}$ fluoroalkyl, —(CH$_2$)$_j$—O—$C_{1-6}$ fluoroalkyl, COR$_a$, CN or NR$_{10}$R$_{11}$ group, or a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different $R_c$ groups, $R_a$, $R_d$ and $R_f$ are identical or different and represent a $C_{1-6}$ alkyl, $C_{1-6}$ alkyloxy or NR$_{12}$R$_{13}$ group, $R_b$, $R_c$ and $R_e$ are identical or different and represent a halogen, or a $C_{1-6}$ alkyl, $C_{3-7}$ cycloalkyl, $C_{1-6}$ alkyloxy, —S(O)$_k$—$C_{1-6}$ alkyl, $C_{1-6}$ fluoroalkyl, $C_{1-6}$ fluoroalkyloxy, —(CH$_2$)$_g$—$C_{3-7}$ cycloalkyl, OH, —(CH$_2$)$_g$—$C_{3-7}$ cycloalkyl, $C_{1-6}$ alkyl-OH, —(CH$_2$)$_g$—$C_{1-6}$ alkyloxy, —(CH$_2$)$_g$—$C_{1-6}$ fluoroalkyl, —(CH$_2$)$_w$—O—$C_{1-6}$ fluoroalkyl, COR$_f$, CN or NR$_{14}$R$_{15}$ group, $R_8$, $R_{8'}$, $R_9$, $R_{9'}$, $R_{10}$, $R_{11}$, $R_{12}$, $R_{13}$, $R_{14}$ and $R_{15}$ are identical or different and represent a hydrogen atom, or a $C_{1-6}$ alkyl, $C_{3-7}$ cycloalkyl, —(CH$_2$)$_h$—$C_{3-7}$ cycloalkyl or —(CH$_2$)$_h$—$C_{1-6}$ fluoroalkyl group.

Optionally, the $R_8$ and $R_9$ groups can form, with the nitrogen atom which bears them, a heterocycle such as: azetidine, pyrrolidine, piperidine, azepane, morpholine or piperazine.
Optionally, the $R_{8'}$ and $R_{9'}$ groups can form, with the nitrogen atom which bears them, a heterocycle such as: azetidine, pyrrolidine, piperidine, azepane, morpholine or piperazine.
Optionally, the $R_{10}$ and $R_{11}$ groups can form, with the nitrogen atom which bears them, a heterocycle such as: azetidine, pyrrolidine, piperidine, azepane, morpholine or piperazine.
Optionally, the $R_{12}$ and $R_{13}$ groups can form, with the nitrogen atom which bears them, a heterocycle such as: azetidine, pyrrolidine, piperidine, azepane, morpholine or piperazine.
Optionally, the $R_{14}$ and $R_{15}$ groups can form, with the nitrogen atom which bears them, a heterocycle such as: azetidine, pyrrolidine, piperidine, azepane, morpholine or piperazine, g, h, i, n, q and t are different or identical and are equal to 1, 2 or 3, k, l, m and v are different or identical and are equal to 0, 1 or 2, j, p, r, u and w are different or identical and are equal to 2, 3 or 4, and also the pharmaceutically acceptable salts, solvates or hydrates thereof and the conformers or rotamers thereof.

The compounds of formula (I) may comprise one or more asymmetric carbon atoms. They may thus exist in the form of a mixture of enantiomers or of diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention. These salts are advantageously prepared with pharmaceutically acceptable acids, but the salts of other acids that are useful, for example for purifying or isolating the compounds of formula (I), also form part of the invention. These acids may be, for example, picric acid, oxalic acid or an optically active acid, for example a tartaric acid, a dibenzoyltartaric acid, a mandelic acid or a camphorsulphonic acid, and those that form physiologically acceptable salts, such as hydrochloride, hydrobromide, sulphate, hydrogen sulphate, dihydrogen phosphate, maleate, fumarate, 2-naphthalenesulfonate or para-toluenesulphonate. For a review of physiologically acceptable salts, see the Handbook of Pharmaceutical Salts: Properties, Selection and Use by Stahl and Wermuth (Wiley-VCH, 2002).

The solvates or hydrates may be obtained directly after the synthesis process, compound (1) being isolated in the form of a hydrate, for example a monohydrate or hemihydrate, or of a solvate of the reaction or purification solvent.

In the context of the invention, the following definitions apply:

$C_{b-c}$ in which b and c may take values from 1 to 9: a carbon-based chain of b to c carbon atoms, for example $C_{1-6}$ is a carbon-based chain that may contain from 1 to 6 carbon atoms, alkyl: a linear or branched, saturated aliphatic group, for example a $C_{1-6}$ alkyl group represents a linear or branched carbon-based chain of 1 to 6 carbon atoms, for example a methyl, ethyl, propyl, isopropyl, butyl, isobutyl, tert-butyl, pentyl or hexyl, cycloalkyl: a cyclic, optionally branched, saturated carbon-based chain containing from 3 to 7 carbon atoms. By way of example, a $C_{3-7}$ cycloalkyl group represents a carbon-based chain of 3 to 7 carbon atoms, for example a cyclopropyl, cyclobutyl, cyclopentyl, cyclohexyl or cycloheptyl, heterocycle: a cyclic or bicyclic, saturated or unsaturated hydrocarbon-based chain comprising one or more heteroatoms chosen from O, S and N, heteroaryl: an aromatic heterocycle, for example a pyridinyl, pyrazinyl, pyrimidinyl, pyridazinyl, triazinyl, pyrazolyl, isooxazolyl, oxadiazolyl, thiazolyl, thiadiazolyl, triazolyl or imidazolyl group, halogen: a fluorine, chlorine or bromine atom, alkyloxy: an —O-alkyl group, alkylthio: a —S-alkyl group, fluoroalkyl: an alkyl group in which one or more hydrogen atoms have been replaced with a fluorine atom, fluoroalkyloxy: an alkyloxy group in which one or more hydrogen atoms have been replaced with a fluorine atom.

Preference is given to group (A) of the compounds of formula (I) defined above, in which the $R_1$ group represents a halogen, or a methyl, ethyl, isopropyl, trifluoromethyl, nitrile, nitro, methoxy, ethoxy, isopropoxy, thiomethyl, thioethyl or thioisopropyl group, and more particularly such that $R_1$ represents a halogen, or a methoxy, ethoxy, thiomethyl, thioethyl ou trifluoromethyl group;

Group (B) of the compounds of formula (I) of which the $R_1$ substituent is defined above or in the preferred group (A) and such that the $R_2$ group is a hydrogen atom.

Particular preference is given to group (C) of the compounds of formula (I) of which the $R_1$ and $R_2$ substituents are defined above or in the preferred groups (A) or (B) and such that the $R_3$ group is a hydrogen atom or a $C_{1-6}$ alkyl group.

The compounds below, and the pharmaceutically acceptable salts, solvates and hydrates thereof, and the conformers or rotamers thereof, are particularly preferred:

2-[(5-Bromopyridin-3-ylamino)methyl]phenol
2-[(5-Bromopyridin-3-ylamino)methyl]-3-fluorophenol
2-[(5-Bromopyridin-3-ylamino)methyl]-4-fluorophenol
2-[(5-Methylpyridin-3-ylamino)methyl]phenol
2-[(5-Bromopyridin-3-ylamino)methyl]-5-fluorophenol
2-[(5-Bromopyridin-3-ylamino)methyl]-3,5-dichlorophenol
2-[(5-Bromopyridin-3-ylamino)methyl]-4-chlorophenol
2-[(5-Bromopyridin-3-ylamino)methyl]-4,6-difluorophenol
2-[1-(5-Bromopyridin-3-ylamino)propyl]phenol
2-[1-(5-Bromopyridin-3-ylamino)ethyl]-4-fluorophenol
2-[(5-Methoxypyridin-3-ylamino)methyl]phenol
2-[1-(5-Bromopyridin-3-ylamino)ethyl]phenol
2-[(5-Bromopyridin-3-ylamino)methyl]-3,4-difluorophenol
5-(2-Hydroxybenzylamino)nicotinonitrile
2-[(5-Chloropyridin-3-ylamino)methyl]phenol
2-[1-(5-Bromopyridin-3-ylamino)butyl]phenol
2-[1-(5-Bromopyridin-3-ylamino)pentyl]phenol
2-[(5-Bromo-6-methylpyridin-3-ylamino)methyl]phenol
2-[(5-Bromo-6-methoxypyridin-3-ylamino)methyl]phenol
5-(2-Hydroxybenzylamino)-3-methylpyridine-2-carbonitrile
2-[(6-Methoxy-5-methylpyridin-3-ylamino)methyl]phenol
2-[(6-Chloro-5-methylpyridin-3-ylamino)methyl]phenol
2-[(6-Bromo-5-methylpyridin-3-ylamino)methyl]phenol
2-[(5,6-Dimethylpyridin-3-ylamino)methyl]phenol
2-[(5-Methyl-6-trifluoromethylpyridin-3-ylamino)methyl]phenol.

A subject of the invention is also a process for preparing the compounds of general formula (I).

In accordance with the invention, the compounds of formula (I) may be prepared according to the general process described in Scheme 1 below.

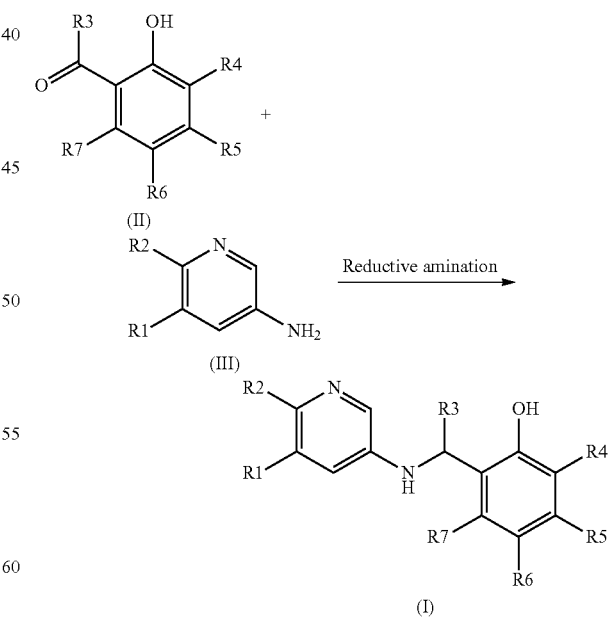

The phenolic compounds of formula (I) in which $R_1$, $R_2$, $R_3$, $R_4$, $R_5$, $R_6$ and $R_7$ are as defined above can be prepared by means of a reductive amination reaction between an aldehyde or a benzyl ketone (II) and an amine (III) in the presence of a reducing agent, such as, for example, and in a non-limiting manner, sodium triacetoxyborohydride, in a solvent such as dichloromethane, according to Scheme 1 and by analogy with the reactions described, for example, in *Org. Pro. R. & D.* (2006) 971-1031.

The functional groups that may be present in the reaction intermediates used in the process may be protected, either permanently or temporarily, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", published by McOmie J. W. F., Plenum Press, 1973, in "Protective Groups in Organic Synthesis", 2nd edition, Greene T. W. and Wuts P. G. M., published by John Wiley & Sons, 1991, and in "Protecting Groups", Kocienski P. J., 1994, Georg Thieme Verlag.

The products which are subjects of the present invention have advantageous pharmacological properties; it was in particular noted that they modulate androgen receptor activity.

Tests given in the experimental section illustrate this androgen receptor-modulating activity. The products which are subjects of the present invention exhibit partial or total antagonist or agonist activities. Because of this activity, the products of the invention can be used as medicaments in humans or animals.

These properties make the products of general formula (I) of the present invention usable as medicaments for treating hormone-dependent cancers such as prostate cancer or breast cancer, and also for combating benign prostatic hyperplasia, early puberty, virilization, polycystic ovary syndrome, Stein-Leventhal syndrome, loss of libido, or endometriosis. The compounds exhibiting partial or total agonist activity can in particular be used for treating afflictions such as loss of muscle mass (sarcopenia), muscle atrophy, impotence and male sterility, abnormal male differentiation (hermaphroditism), hypogonadism or osteoporosis. The products of general formula (I) of the invention also find their cosmetic use for body or hair hygiene.

The products of general formula (I) of the invention also find their use in the treatment of hirsutism, acne, seborrhoea, oily skin, androgenic alopecia or hyperpilosity, and they can be used for the production of a medicament for preventing and/or treating hirsutism, androgenic alopecia, hyperpilosity, atopic dermatitis, or sebaceous gland disorders such as hyperseborrhoea, acne, oily skin or seborrhoeic dermatitis. The products of formula (I) can therefore be used in dermatology: they can be used alone or in combination. They can be combined in particular with an antibiotic product, such as derivatives of azelaic acid, fusidic acid or erythromycin or with a retinoid derivative such as tretinoin for the treatment of acne, or with a 5a-reductase inhibitor such as (5alpha,17beta)-N-1, 1-dimethylethyl-3-oxo-4-azaandrost-1-ene-17-carboxamide (or Finasteride, Merck, 13th Edition) or azelaic acid or an androgen receptor-blocking agent for the treatment of acne, alopecia or hirsutism, or with a product that stimulates hair growth, such as Minoxidil, for the treatment of alopecia.

A subject of the present invention is also, as medicaments, the compounds of formula (I) as described above, and also the pharmaceutically acceptable salts and pharmaceutically acceptable solvates and/or hydrates thereof.

PROCEDURES

Example 1

2-[(5-Bromopyridin-3-ylamino)methyl]phenol 295 mg (1.4 mmol, 1.4 eq) of sodium triacetoxyborohydride are added to a solution of 173 mg (1 mmol, 1 eq) of 5-bromopyridin-3-ylamine (starting material 1) and 122 mg (1 mmol, 1 eq) of 2-hydroxybenzaldehyde (starting material 2) in 20 ml of dichloromethane. The solution is stirred at room temperature for 24 h. The medium is poured into water and stirred for 2 h. The aqueous phase is extracted with dichloromethane. The organic phases are combined, washed with water, and then dried over sodium sulphate. The residue is chromatographed on silica gel (80/20 heptane/ethyl acetate). 2-[(5-Bromopyridin-3-ylamino)methyl]phenol is obtained in the form of a white solid.

Melting point=184° C.

1H NMR (DMSO) 4.19 (d, 2H, J=5.8 Hz); 6.62-6.65 (m, 1H); 6.74 (t, 1H, J=7.4 Hz); 6.82-6.84 (d, 1H, J=9.0 Hz); 7.05-7.09 (m, 2H); 7.15-7.17 (d, 1H, J=8.8 Hz); 7.77 (s, 1H); 7.95 (s, 1H); 9.62 (s, 1H).

Examples 2 to 15

Examples 2 to 15 are described in Table 1 below. The compounds are synthesized according to the procedures described above, replacing the starting materials 1 and 2 mentioned in Example 1 with the products mentioned in Table 1.

TABLE 1

| Example # | IUPAC name | Starting material 1 | Starting material 2 | Melting point (° C.) | $^1$H NMR - 400 MHz (s = singlet, d = doublet, t = triplet, m = multiplet, q = quartet, J = coupling constant in Hz) |
|---|---|---|---|---|---|
| 2 | 2-[(5-Bromopyridin-3-ylamino)methyl]-3-fluorophenol | 5-Bromopyridin-3-ylamine | 2-Fluoro-6-hydroxybenzaldehyde | 193-195 | (DMSO) 4.17-4.19 (d, 2H, J = 4.8 Hz); 6.43-6.46 (m, 1H); 6.64 (t, 1H, J = 8.6 Hz); 6.7 (d, 1H, J = 8.2 Hz); 7.10-7.16 (m, 1H); 7.24 (s, 1H); 7.77 |

TABLE 1-continued

| Example # | IUPAC name | Starting material 1 | Starting material 2 | Melting point (° C.) | $^1$H NMR - 400 MHz (s = singlet, d = doublet, t = triplet, m = multiplet, q = quartet, J = coupling constant in Hz) |
|---|---|---|---|---|---|
| 3 | 2-[(5-Bromopyridin-3-ylamino)methyl]-4-fluorophenol | 5-Bromopyridin-3-ylamine | 5-fluoro-2-hydroxybenzaldehyde | 192-194 | (DMSO) 4.2 (d, 2H, J = 6.0 Hz); 6.67-6.7 (m, 1H); 6.80-6.83 (m, 1H); 6.87-6.92 (m, 1H); 6.95-6.98 (m, 1H); 7.07-7.11 (m, 1H); 7.80 (s, 1H); 7.95 (s, 1H); 9.67 (s, 1H) |
| 4 | 5-(2-Hydroxybenzylamino)nicotinonitrile | 5-Aminonicotinonitrile | 2-Hydroxybenzaldehyde | not determined | (DMSO) 4.22 (d, 2H, J = 4.8 Hz); 6.82 (t, 1H, J = 7.4 Hz); 6.83-6.85 (m, 2H); 7.08 (t, 1H, J = 7.7); 7.17 (d, 1H, J = 7.4 Hz); 7.23 (s, 1H); 8.07 (s, 1H); 8.24 (s, 1H); 9.68 (s, 1H) |
| 5 | 2-[(5-Bromopyridin-3-ylamino)methyl]-5-fluorophenol | 5-Bromopyridin-3-ylamine | 4-Fluoro-2-hydroxybenzaldehyde | 172 | (CD3OD) 4.27 (s, 2H); 6.50-6.58 (m, 2H); 7.16-7.25 (m, 2H); 7.77 (s, 1H); 7.88 (s, 1H) |
| 6 | 2-[(5-Bromopyridin-3-ylamino)methyl]-3,5-dichlorophenol | 5-Bromopyridin-3-ylamine | 2,4-Dichloro-6-hydroxybenzaldehyde | 182 | (DMSO) 4.22 (d, 2H, J = 4.8 Hz); 6.36-6.38 (m, 1H); 6.88 (s, 1H); 7.06 (s, 1H); 7.26 (s, 1H); 7.79 (s, 1H); 8.03 (s, 1H); 10.83 (s, 1H) |
| 7 | 2-[(5-Bromopyridin-3-ylamino)methyl]-4-chlorophenol | 5-Bromopyridin-3-ylamine | 5-Chloro-2-hydroxybenzaldehyde | 226-228 | (CD3OD) 4.29 (s, 2H); 6.79 (d, 1H, J = 8.6 Hz); 7.07 (m, 1H); 7.16-7.24 (m, 2H); 7.80 (s, 1H); 7.88 (s, 1H) |
| 8 | 2-[(5-Bromopyridin-3-ylamino)methyl]-4,6-difluorophenol | 5-Bromopyridin-3-ylamine | 3,5-Difluoro-2-hydroxybenzaldehyde | not determined | (DMSO) 4.27 (s, 2H); 6.73 (m, 1H); 6.86 (d, 1H, J = 9.2 Hz); 7.06-7.12 (m, 2H); 7.81 (s, 1H); 7.94 (s, 1H); 9.81 (s, 1H) |
| 9 | 2-[1-(5-Bromopyridin-3-ylamino)propyl]phenol | 5-Bromopyridin-3-ylamine | 1-(2-Hydroxyphenyl)propan-1-one | 215-217 | (CH3OD) 0.97 (t, 3H); 1.84 (m, 2H); 4.6 (t, 1H); 6.75 (m, 2H); 7-7.2 (m, 3H); 7.67 (s, 1H); 7.81 (s, 1H) |

TABLE 1-continued

| Example # | IUPAC name | Starting material 1 | Starting material 2 | Melting point (° C.) | $^1$H NMR - 400 MHz (s = singlet, d = doublet, t = triplet, m = multiplet, q = quartet, J = coupling constant in Hz) |
|---|---|---|---|---|---|
| 10 | 2-[1-(5-Bromopyridin-3-ylamino)ethyl]-4-fluorophenol | 5-Bromopyridin-3-ylamine | 1-(5-Fluoro-2-hydroxyphenyl)ethanone | 175-177 | (DMSO) 1.38 (d, 3H, J = 6.7 Hz); 4.67-4.73 (m, 1H); 6.74-6.96 (m, 5H); 7.76 (s, 1H); 7.83 (s, 1H); 9.72 (s, 1H) |
| 11 | 2-[(5-Methoxypyridin-3-ylamino)methyl]phenol | 5-Methoxypyridin-3-ylamine | 2-Hydroxybenzaldehyde | 188-190 | (DMSO) 3.70 (s, 3H); 4.18 (d, 2H, J = 5.4 Hz); 6.30-6.33 (m, 1H); 6.46 (d, 1H, J = 4.6 Hz); 6.73 (t, 1H, J = 7.4 Hz); 6.82 (d, 1H, J = 7.4 Hz); 7.03-7.07 (m, 1H); 7.17 (d, 1H, J = 7.4 Hz); 7.46 (s, 1H); 7.60 (s, 1H); 9.59 (s, 1H) |
| 12 | 2-[1-(5-Bromopyridin-3-ylamino)ethyl]phenol | 5-Bromopyridin-3-ylamine | 2'-Hydroxyacetophenone | 178-180 | (DMSO) 1.38 (d, 3H, J = 6.7 Hz); 4.68-4.75 (m, 1H); 6.70-6.76 (m, 2H); 6.81 (d, 1H, J = 8.0 Hz); 6.87 (d, 1H, J = 4.2 Hz); 7.02 (t, 1H, J = 7.9 Hz); 7.15 (d, 1H, J = 9.0 Hz); 7.72 (s, 1H); 7.83 (s, 1H); 9.63 (s, 1H) |
| 13 | 2-[(5-Bromopyridin-3-ylamino)methyl]-3,4-difluorophenol | 5-Bromopyridin-3-ylamine | 5-6-Difluoro-2-hydroxybenzaldehyde | 194-196 | (CD3OD) 4.37 (s, 2H); 6.57-6.61 (m, 1H); 6.97-7.03 (m, 1H); 7.37 (s, 1H); 7.77 (s, 1H); 7.96 (s, 1H) |
| 14 | 2-[(5-Methylpyridin-3-ylamino)methyl]phenol | 5-Methylpyridin-3-ylamine | 2-Hydroxybenzaldehyde | 183-185 | (DMSO) 2.13 (s, 3H); 4.18 (d, 2H, J = 5.8 Hz); 6.15-6.18 (m, 1H); 6.70-6.75 (m, 2H); 6.82 (d, 1H, J = 8 Hz); 7.05 (t, 1H, J = 7.7 Hz); 7.16 (d, 1H, J = 7.4 Hz); 7.57 (s, 1H); 7.77 (s, 1H); 9.55 (s, 1H) |
| 15 | 2-[(5-Chloropyridin-3-ylamino)methyl]phenol | 5-Chloropyridin-3-ylamine | 2-Hydroxybenzaldehyde | 231-213 | (DMSO) 4.36 (d, 2H, J = 5.8 Hz); 6.55 (d, 1H, J = 5.5 Hz); 6.60 (s, 1H); 6.74 (t, 1H, |

TABLE 1-continued

| Example # IUPAC name | Starting material 1 | Starting material 2 | Melting point (° C.) | $^1$H NMR - 400 MHz (s = singlet, d = doublet, t = triplet, m = multiplet, q = quartet, J = coupling constant in Hz) |
|---|---|---|---|---|
| | | | | J = 7.4 Hz); 7.15 (d, 1H, J = 7.3 Hz); 7.22-7.24 (m, 1H); 7.92 (d, 1H, J = 5.5 Hz); 9.82 (s, 1H) |

All the NMR (nuclear magnetic resonance) spectra are in accordance with the proposed structures. The chemical shifts are expressed in parts per million. The internal reference is tetramethylsilane. The following abbreviations are used: CDCl3 = deuterated chloroform, DMSO = deuterated dimethyl sulphoxide, CD3OD = deuterated methanol.

Example 16

Biological Tests

The compounds according to the invention show inhibitory properties on receptors of AR type. This AR receptor-inhibiting activity is measured in a transactivation test through the KdR (resting), KdA (active) and Kdapp (apparent) dissociation constants according to the method set out in *J. Molecular Biology* (1965), 12(1), 88-118, Monod J. et al.

The expression "AR-type receptor inhibitor" means, according to the invention, any compound which has a Kdapp dissociation constant of less than or equal to 1 µM, and a KdR/Kda ratio ≤10, in a transactivation test.

The preferred compounds of the present invention have a dissociation constant of less than or equal to 500 nM and advantageously less than or equal to 100 nM.

The transactivation test is carried out in the PALM (PC3 Androgen receptor Luciferase MMTV) cell line which is a stable transfectant containing the PMMTV-neo-Luc (reporter gene) and pSG5puro-AR plasmids.

In this study, the affinity of each product for the 2 receptor states (KdR and KdA) is determined, as is an apparent Kd (Kdpp). This constant is a result of the 2 Kd, but also depends on the initial equilibrium of the receptor between the active state and the resting state ($L_0$) and on its expression level. It is determined by means of the following formula:

$$1/KdApp=(L0/(1+L0))x(1/KdR)+(1/(1+L0))x(1/KdA)$$

To determine these constants, "cross curves" of the test product against a reference agonist, methyltrienolone, are produced in 96-well plates. The test product is used at 10 concentrations and the reference agonist at 7 concentrations.

By way of illustration, a Kdapp of 6 nM is obtained for the compound (1), a Kdapp of 5 nM is obtained for the compound (2), a Kdapp of 200 nM is obtained for the compound (4), a Kdapp of 60 nM is obtained for the compound (9) and a Kdapp of 15 nM is obtained for the compound (14).

The invention claimed is:
1. A compound of formula (I):

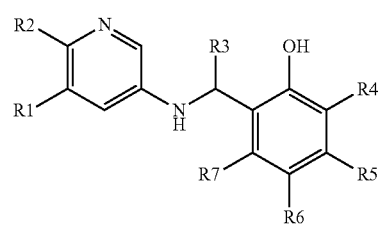

(I)

in which:
$R_1$ represents a $C_{1-6}$ alkyl, $C_{3-7}$ cycloalkyl, $C_{1-6}$ alkyloxy, —S(O)$_m$—C$_{1-8}$ alkyl, $C_{1-6}$ fluoroalkyl, $C_{1-6}$ fluoroalkyloxy, —(CH$_2$)$_n$—C$_{3-9}$ cycloalkyl, $C_{2-6}$ alkyl-OH, —(CH$_2$)$_n$—C$_{1-6}$ alkyloxy, —(CH$_2$)$_n$—C$_{1-6}$ fluoroalkyl, —(CH$_2$)$_p$—O—C$_{1-6}$ fluoroalkyl, COR$_a$, CN, NO$_2$ or NR$_8$R$_9$ group, a halogen or a phenyl group; wherein the phenyl group can optionally be substituted with one to three identical or different R$_b$ groups;

$R_2$ represents a $C_{1-6}$ alkyl, $C_{3-7}$ cycloalkyl, $C_{1-6}$ alkyloxy, —S(O)$_v$—C$_{1-6}$ alkyl, $C_{1-6}$ fluoroalkyl, $C_{1-6}$ fluoroalkyloxy, —(CH$_2$)$_q$—C$_{3-9}$ cycloalkyl, $C_{2-6}$ alkyl-OH, —(CH$_2$)$_q$—C$_{1-6}$ alkyloxy, —(CH$_2$)$_q$—C$_{1-6}$ fluoroalkyl, —(CH$_2$)$_r$—O—C$_{1-6}$ fluoroalkyl, COR$_d$, ON, NO$_2$ or NR$_8$'R$_9$' group, a hydrogen atom, a halogen or a phenyl group; wherein the phenyl group can optionally be substituted with one to three identical or different R$_e$ groups;

$R_3$ represents a hydrogen atom or a $C_{1-9}$ alkyl, $C_{3-9}$ cycloalkyl, $C_{1-6}$ fluoroalkyl, —(CH$_2$)$_t$—C$_{3-9}$ cycloalkyl, —C$_{2-6}$ alkyl-OH, —(CH$_2$)$_u$—C$_{1-6}$ alkyloxy, —(CH$_2$)$_t$—C$_{3-7}$ cycloalkyl, fluoroalkyl, or —(CH$_2$)$_u$—O—C$_{1-6}$ fluoroalkyl group;

$R_4$, $R_5$, $R_6$ and $R_7$ are identical or different and represent either a hydrogen atom or a $C_{1-6}$ alkyl, $C_{3-7}$ cycloalkyl, $C_{1-6}$ alkyloxy, —S(O)$_i$—C$_{1-6}$ alkyl, $C_{1-6}$ fluoroalkyl, $C_{1-6}$ fluoroalkyloxy, —(CH$_2$)$_i$—C$_{3-9}$ cycloalkyl, $C_{1-6}$ alkyl-OH, —(CH$_2$)$_i$—C$_{1-6}$ alkyloxy, —(CH$_2$)$_i$—C$_{1-6}$ fluoroalkyl, —(CH$_2$)$_j$—O—C$_{1-6}$ fluoroalkyl, COR$_a$, ON or NR$_{10}$R$_{11}$ group, a halogen or a phenyl group wherein the phenyl group can optionally be substituted with one to three identical or different R$_c$ groups;

$R_a$, $R_d$ and $R_f$ are identical or different and represent a $C_{1-6}$ alkyl, $C_{1-6}$ alkyloxy or NR$_{12}$R$_{13}$ group;

$R_b$ represents a halogen, or a $C_{1-6}$ alkyl, $C_{3-7}$ cycloalkyl, $C_{1-6}$ alkyloxy, $-S(O)_k-C_{1-6}$ alkyl, $C_{1-6}$ fluoroalkyl, $C_{1-6}$ fluoroalkyloxy, $-(CH_2)_g-C_{3-7}$ cycloalkyl, $C_{1-6}$ alkyl-OH, $-(CH_2)_g-C_{1-6}$ alkyloxy, $-(CH_2)_g-C_{1-6}$ fluoroalkyl, $-(CH_2)_w-O-C_{1-6}$ fluoroalkyl, $COR_f$, ON or $NR_{14}R_{15}$ group;

$R_c$ and $R_e$ are identical or different and represent a halogen, or a $C_{1-6}$ alkyl, $C_{3-7}$ cycloalkyl, $C_{1-6}$ alkyloxy, $-S(O)_k-C_{1-6}$ alkyl, $C_{1-6}$ fluoroalkyl, $C_{1-6}$ fluoroalkyloxy, $-(CH_2)_g-C_{3-7}$ cycloalkyl, OH, $C_{1-6}$ alkyl-OH, $-(CH_2)_g-C_{1-6}$ alkyloxy, $-(CH_2)_g-C_{1-6}$ fluoroalkyl, $-(CH_2)_w-O-C_{1-6}$ fluoroalkyl, $COR_f$, ON or $NR_{14}R_{15}$ group;

$R_8, R_{8'}, R_9, R_{10}, R_{11}, R_{12}, R_{13}, R_{14}$ and $R_{15}$ are identical or different and represent a hydrogen atom, or a $C_{1-6}$ alkyl, $C_{3-7}$ cycloalkyl, $-(CH_2)_h-C_{3-7}$ cycloalkyl or $-(CH_2)_h-C_{1-6}$ fluoroalkyl group;

optionally, the $R_8$ and $R_9$ groups can form, with the nitrogen atom which bears them, a heterocycle;

under the proviso that when $R_1$ represents a halogen, and the halogen is bromine, at least one of $R_2, R_3, R_4, R_5, R_6$, and $R_7$ are not a hydrogen;

optionally, the $R_{8'}$ and $R_{9'}$ groups can form, with the nitrogen atom which bears them, a heterocycle, optionally, the $R_{10}$ and $R_{11}$ groups can form, with the nitrogen atom which bears them, a heterocycle;

optionally, the $R_{12}$ and $R_{13}$ groups can form, with the nitrogen atom which bears them, a heterocycle;

optionally, the $R_{14}$ and $R_{15}$ groups can form, with the nitrogen atom which bears them, a heterocycle;

g, h, i, n, q and t are different or identical and are equal to 1, 2 or 3, k, l, m and v are different or identical and are equal to 0, 1 or 2, j, p, r, u and w are different or identical and are equal to 2, 3 or 4, or a pharmaceutically acceptable salt thereof.

2. The compound as defined by claim 1, wherein:
$R_1$ represents a halogen, a methyl, an ethyl, an isopropyl, a trifluoromethyl, a nitrile, a nitro, a methoxy, an ethoxy, an isopropoxy, a thiomethyl, a thioethyl, or a thioisopropyl group.

3. The compound as defined by claim 2, wherein the $R_1$ group represents a halogen, a methoxy, an ethoxy, a thiomethyl, a thioethyl or a trifluoromethyl group.

4. The compound as defined by claim 1, wherein the $R_2$ group is a hydrogen atom.

5. The compound as defined by claim 1 wherein the $R_3$ group is a hydrogen atom or a $C_{1-6}$ alkyl group.

6. The compound as defined by claim 1, wherein the compound is selected from the group consisting of:
2-[(5-Bromopyridin-3-ylamino)methyl]-3-fluorophenol;
2-[(5-Bromopyridin-3-ylamino)methyl]-4-fluorophenol;
2-[(5-Methylpyridin-3-ylamino)methyl]phenol;
2-[(5-Bromopyridin-3-ylamino)methyl]-5-fluorophenol;
2-[(5-Bromopyridin-3-ylamino)methyl]-3,5-dichlorophenol;
2-[(5-Bromopyridin-3-ylamino)methyl]-4-chlorophenol;
2-[(5-Bromopyridin-3-ylamino)methyl]-4,6-difluorophenol;
2-[1-(5-Bromopyridin-3-ylamino)propyl]phenol;
2-[1-(5-Bromopyridin-3-ylamino)ethyl]-4-fluorophenol;
2-[(5-Methoxypyridin-3-ylamino)methyl]phenol;
2-[1-(5-Bromopyridin-3-ylamino)ethyl]phenol;
2-[(5-Bromopyridin-3-ylamino)methyl]-3,4-difluorophenol;
5-(2-Hydroxybenzylamino)nicotinonitrile;
2-[(5-Chloropyridin-3-ylamino)methyl]phenol;
5-(2-Hydroxybenzylamino)nicotinonitrile;
2-[1-(5-Bromopyridin-3-ylamino)butyl]phenol;
2-[1-(5-Bromopyridin-3-ylamino)pentyl]phenol;
2-[(5-Bromo-6-methylpyridin-3-ylamino)methyl]phenol;
2-[(5-Bromo-6-methoxypyridin-3-ylamino)methyl]phenol;
5-(2-Hydroxybenzylamino)-3-methylpyridine-2-carbonitrile;
2-[(6-Methoxy-5-methylpyridin-3-ylamino)methyl]phenol;
2-[(6-Chloro-5-methylpyridin-3-ylamino)methyl]phenol;
2-[(6-Bromo-5-methylpyridin-3-ylamino)methyl]phenol;
2-[(5,6-Dimethylpyridin-3-ylamino)methyl]phenol; and
2-[(5-Methyl-6-trifluoromethylpyridin-3-ylamino)methyl]phenol,
and a pharmaceutically acceptable salt thereof.

7. A medicament comprising the compound as defined by claim 1.

8. A method for treating hirsutism, androgenic alopecia, hyperseborrhoea, acne, oily skin or seborrhoeic dermatitis, said method comprising administering to a subject in need of such treatment an effective amount of a compound as defined by claim 1.

9. A method for treating acne, said method comprising administering to a subject in need of treatment an effective amount of a compound as defined by claim 1 for treating acne.

10. The compound as defined by claim 1, wherein the $R_5$ and $R_9$ groups can form azetidine, pyrrolidine, piperidine, azepane, morpholine or piperazine.

11. The compound as defined by claim 1, wherein the $R_{8'}$ and $R_{9'}$ groups can form azetidine, pyrrolidine, piperidine, azepane, morpholine or piperazine.

12. The compound as defined by claim 1, wherein the $R_{10}$ and $R_11$ groups can form azetidine, pyrrolidine, piperidine, azepane, morpholine or piperazine.

13. The compound as defined by claim 1, wherein the $R_{12}$ and $R_{13}$ groups can form azetidine, pyrrolidine, piperidine, azepane, morpholine or piperazine.

14. The compound as defined by claim 1, wherein the $R_{14}$ and $R_{15}$ groups can form azetidine, pyrrolidine, piperidine, azepane, morpholine or piperazine.

* * * * *